United States Patent [19]

Synovec et al.

[11] Patent Number: 4,875,169

[45] Date of Patent: Oct. 17, 1989

[54] METHOD FOR IMPROVING THE LIMIT OF DETECTION IN A DATA SIGNAL

[75] Inventors: Robert E. Synovec; Edward S. Yueng, both of Ames, Iowa

[73] Assignee: Iowa State University Research Foundation, Inc., Ames, Iowa

[21] Appl. No.: 201,304

[22] Filed: May 27, 1988

Related U.S. Application Data

[63] Continuation of Ser. No. 851,129, Apr. 11, 1986, abandoned.

[51] Int. Cl.[4] .................. G06F 15/20; G01N 31/08
[52] U.S. Cl. ..................... 364/497; 364/498; 364/574; 73/23.1; 73/61.1 C
[58] Field of Search ............... 364/497, 498, 571, 573, 364/574; 73/23.1, 61.1 C

[56] References Cited

U.S. PATENT DOCUMENTS

| | | | |
|---|---|---|---|
| 3,506,818 | 4/1970 | Smith | 73/23.1 |
| 3,733,474 | 5/1973 | Edwards et al. | 73/23.1 |
| 3,797,300 | 3/1974 | Sato | 73/23.1 |
| 3,813,532 | 5/1974 | Sato et al. | 235/183 |
| 4,054,384 | 10/1977 | Hawes | 73/23.1 |
| 4,170,893 | 10/1979 | Kleiss | 73/23.1 |
| 4,266,277 | 5/1981 | Issenmann | 73/23.1 |
| 4,307,453 | 12/1981 | Kleiss | 73/23.1 |
| 4,314,343 | 2/1982 | Tomlinson | 364/498 |
| 4,357,668 | 11/1982 | Schwartz et al. | 73/23.1 |
| 4,374,424 | 2/1983 | Coustre et al. | 364/497 |
| 4,455,084 | 6/1984 | Webb, Jr. et al. | 73/61.1 C |
| 4,524,420 | 6/1985 | Glodo et al. | 364/497 |
| 4,546,643 | 10/1985 | Bonneyrat et al. | 364/498 |

OTHER PUBLICATIONS

Phillips, J. B., "Comments on Improvement of the Limit . . . ", *Anal. Chem.*, vol. 58, (1986) 2901–2902.

Synovec, R. E., and Yeung, E. S., "Comparison of an Integration Procedure to Fourier . . . ", *Anal. Chem.*, vol. 58, (1986), pp. 2093–2095.

*Primary Examiner*—Parshotam S. Lall
*Assistant Examiner*—Brian M. Mattson
*Attorney, Agent, or Firm*—Zarley McKee, Thomte, Voorhees & Sease

[57] ABSTRACT

A method for improving the limit of detection for a data set in which experimental noise is uncorrelated along a given abscissa and an analytical signal is correlated to the abscissa, the steps comprising collecting the data set, converting the data set into a data signal including an analytical portion and the experimental noise portion, designating and adjusting a baseline of the data signal to center the experimental noise numerically about a zero reference, and integrating the data signal preserving the corresponding information for each point of the data signal. The steps of the method produce an enhanced integrated data signal which improves the limit of detection of the data signal.

11 Claims, 8 Drawing Sheets

METHOD FOR IMPROVING THE LIMIT OF DETECTION IN A DATA SIGNAL

GRANT REFERENCE

This application was funded at least in part by grants from the Society for Analytical Chemistry, Pittsburgh, Pa.; and the U.S. Department of Energy under Contract No. W-7405-eng-82, with specific support by the Office of Basic Energy Sciences.

This is a continuation of co-pending application Ser. No. 851,129, filed on Apr. 11, 1986, now abandoned.

BACKGROUND OF THE INVENTION a. Field of the Invention

Many scientific or analytical procedures involve the gathering of a set of data by monitoring a process and then converting the results of the gathered data set into a data signal representing the data set. Because extraneous or non-analytical elements are generally involved in the procedures, the complete data signal generally contains both an analytical signal portion and non-relevant, uncorrelated non-analytical signal portions, which will be called noise. The data signal (analytical plus noise portions) usually represents a continuous record of magnitude of the data signal with respect to a parameter such as time, wavelength, frequency, etc. The data signal must be analyzed to derive desired information and conclusions. Because of the noise contained in the data signal, completely precise analysis is many times not possible if the analytical signal is of comparable magnitude to the noise. There is therefore some uncertainty as to the extent the information derived from the data signal by conventional methods is complete and accurate. This is called the limit of detection with respect to the signal.

The present invention relates to a method for improving the limit of detection in a data signal, and in particular, relates to a method of utilizing integration to improve the limit of detection.

b. Problems In The Art

Data signals, when plotted orthogonally (for example magnitude of the signal versus time), visually appear as lines with constantly changing peaks and valleys. Because a complete data signal includes a relevant analytical signal superimposed with the non-relevant noise signal, many times the desired information from the analytical signal is difficult to derive. If the amplitude of the analytical signal is comparable to that of the noise, identifying the salient peaks and valleys of the analytical signal and their relationship to time (or other parameters) represented by the abscissa, can be difficult to achieve. Also, since the noise generally behaves randomly, and can include glitches or other nonrelevant amplitudes, such analytical measures always must contain the qualification of a margin of error, that is a limit of detection.

Close control of experimental environment and procedures helps to improve the limit of detection. A further method to improve the limit of detection is to apply statistical analysis to the derived data in the data signal. While some of these methods have further improved the limit of detection, there is a real need for yet more improvement to allow greater precision and accuracy in analytical methods.

It is therefore a primary object of the present invention to provide a method for improving the limit of detection in a data signal which improves over or solves the present problems in the art.

A further object of the present invention is to provide a method for improving the limit of detection in a data signal which improves the limit of detection between five and twenty times that of present analytical systems.

A further object of the present invention is to provide a method for improving the limit of detection in a data signal which is performed upon the data signal after collection of the data set is completed but which retains all pertinent information with respect to the data set.

Another object of the present invention is to provide a method for improving the limit of detection in a data signal which maximizes enhancement of the analytical portion of the data signal while minimizing, if not eliminating, the noise portion of the data signal.

A further object of the present invention is to provide a method for improving the limit of detection in a data signal which retains all information of the original data signal, does not miss any portion of the analytical signal contained in the data signal, is easy to implement, and does not require any additional procedures, equipment, or restrictions during the analytical procedure. These and other objects, features, and advantages of the present invention will become apparent with reference to the accompanying specification and claims.

SUMMARY OF THE INVENTION

This invention performs mathematical operations upon data included in a data signal derived from an analytical procedure, to increase the detectability of the relevant data. The method of the invention is applicable to a variety of analytical procedures which result in the derivation of a data signal which is comprised of an analytical portion correlated along an abscissa, and having noise which is uncorrelated. Examples of such analytical procedures include, but are not limited to, chromatography, spectral scanning measurements, flow injection analysis, sample injection coupled to atomic absorption spectroscopy, and nuclear magnetic resonance.

The method of the invention operates upon the data signal after it is compiled and therefore all the relevant information from the data gathering is preserved in its correlated form. The present invention improves the accuracy and precision of deriving desired information and conclusions from the data signal by improving the detectability of the analytical portion of the signal, while minimizing any problems caused by uncorrelated noise.

The improvement in detectability of the invention can be alternatively described as limit of detection enhancement.

Every data signal, because of experimental variables and extraneous factors, cannot be susceptible of absolute detectability. Therefore, depending upon the type of analytical procedure being performed, the environment of the procedure, and the handling of the procedure, a limit of detection must be factored into the results to maintain the validity of the results. If the limit of detection is poor, much relevant information from the data signal must necessarily be ignored and is wasted. Additionally, the precision and accuracy of the results derived from the data signal are compromised. In chromatography, for example, limit of detection is defined as the lowest concentration (or mass) of a chemical species that can be determined to be statistically different from an analytical blank (as defined by the International Union of Pure and Applied Chemistry (IUPAC)).

The steps of the method of the present invention for improving the limit of detection for a data signal are as follows, and are performed in the following sequence.

First, the analytical procedure is set up, and run to conclusion. The data set is collected from the analytical procedure. The data set is converted into a data signal. The data signal is comprised of at least two component portions; an analytical portion containing the relevant analytical data and information, and an experimental noise portion containing noncorrelated, non-relevant noise.

Next, a baseline is designated for the data signal. The baseline sets a reference coordinate axis (abscissa or x-axis) for the data signal, and the data signal is correlated to the baseline in two orthogonal directions to the baseline.

The baseline is then adjusted with respect to the data signal to center the experimental noise component of the data signal numerically about what will be called a zero baseline reference.

Finally, the data signal, now having noise centered about zero baseline, is integrated for each point of the data signal. All information regarding the correlation of the data signal to the baseline is preserved and the result of the method is an enhanced integrated data signal with an improved limit of detection for the analytical portion of the signal. Because the experimental noise is numerically centered about the zero baseline reference, integration will not enhance, but rather minimize or "zero-out" the noise, but the correlated, non-random analytical portion is additively summed to increase the detectability of the analytical portion of the data signal from five to twenty times that of the original non-integrated data signal.

The present invention is facilitated by feeding the data set contained in the data signal into a computer which digitizes the information contained in the data signal and performs the required method steps to achieve the base-line-adjusted, integrated data signal. The computer can further identify and quantify the analytical portion of the data signal and store any and all results, including all the correlation values of the data signal, for further operations, visual representation, or print-out.

BRIEF DESCRIPTION OF THE DRAWINGS

FIGS. 1A, B, and C are representative of baseline noise, (A) as typically found, (B) as baseline adjusted around a zero reference, and (C) as integrated.

FIGS. 2A, B, and C are representations of a simulated chromatogram for successive dilutions (A, B, and C) of a sample.

FIGS. 3A, B, and C are representations of the simulated chromatograms of FIG. 2 after integration.

FIGS. 4A, B, and C are representations of integrated chromatograms of the same peak data as FIG. 2C, but with different noise data.

DETAILED DESCRIPTION OF THE PREFERRED EMBODIMENT

It is to be understood that the present invention is applicable to any analytical method in which noise is uncorrelated and an analytical signal is correlated along an abscissa. Examples previously given of areas of application include chromatography, spectral scanning measurements, flow injection analysis, sample injection coupled to atomic absorption spectroscopy, and nuclear magnetic resonance. For the purposes of this application, the present invention will be discussed in terms of a preferred embodiment relating to chromatography but it is to be understood that its application is not limited to chromatography.

Chromatography is a well known in the art analytical method for determining the constituent chemical species of a sample.

By referring to the drawings, a summary of how the method according to the invention operates will be given. Thereafter, more complete details of the invention will be set forth.

The invention is applied to chromatography as follows. Chromatography produces a data signal, called a "chromatogram" which has an analytical signal or portion correlated along an abscissa and non-relevant noise which is uncorrelated to the abscissa. The abscissa is the parameter of time, generally in seconds. The orthogonal ordinant is the parameter of relative signal strength or magnitude of the data signal.

Examples of what chromatograms look like can be found at FIGS. 2A, B, & C. These Figures represent chromatograms of the same sample, except that the sample is successively diluted from FIG. 2A to FIG. 2C. As can be seen, chromatographic peaks 10a–10e, representing the constituent species of the sample, become increasingly hard to detect as the sample is diluted. FIG. 2C shows that when the magnitude of noise is on the same order as the chromatographic peaks, detectability, especially later in time, becomes difficult, if not impossible.

Figure 2:
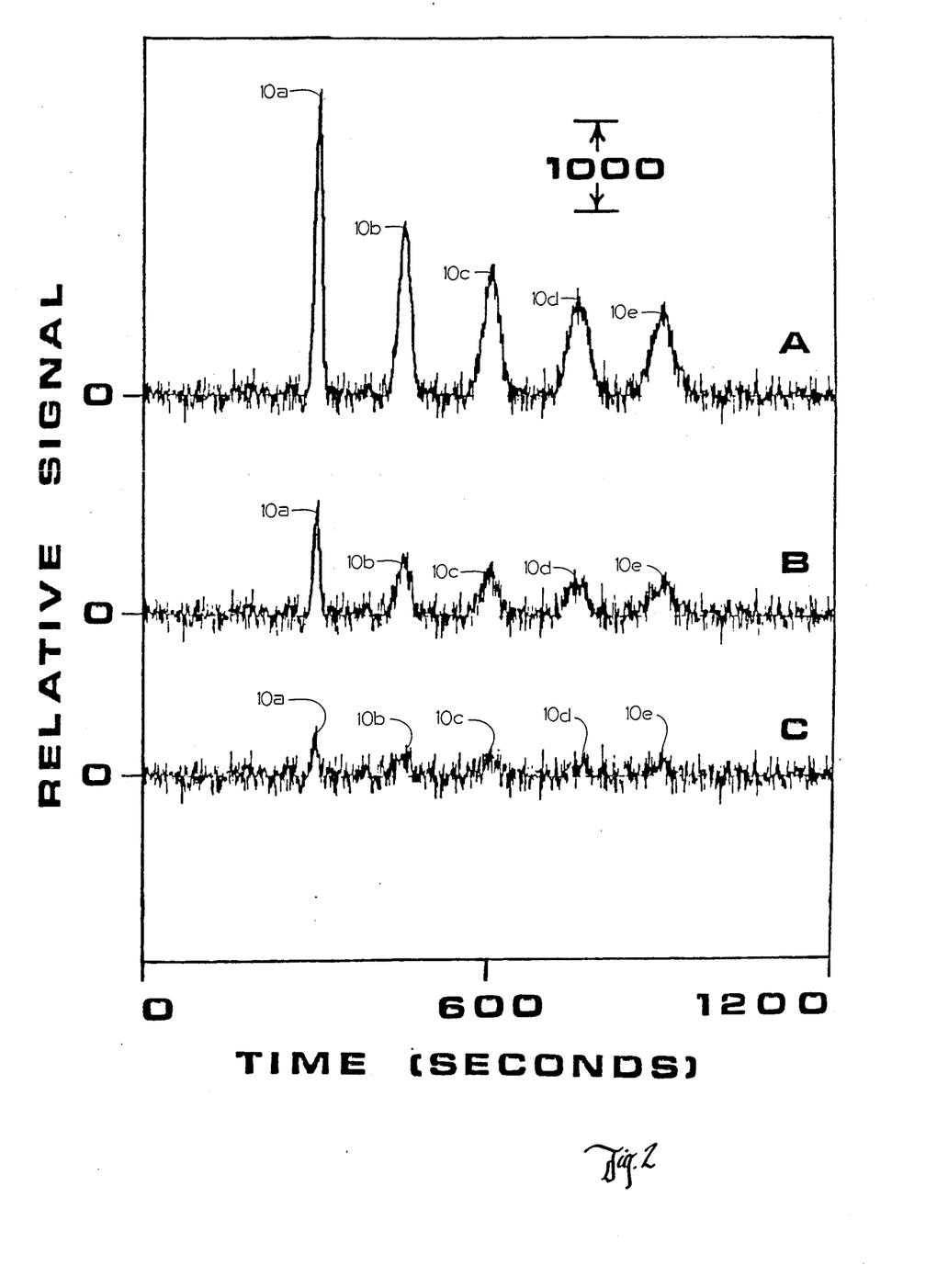

Additionally, as can be seen in chromatographic peaks 10b, c, d, and e of FIGS. 2A–C, (and particularly FIG. 2C) the peaks are not definite and precise so that additional difficulty, even though the general peak shape is discernible, is encountered in determining precisely the peak point with regard to the abscissa. Therefore, the need for improved detectability is exemplified by FIG. 2.

FIG. 2 shows the data signals baseline adjusted along a zeroed abscissa. However, in the chromatographic process, the baseline originally behaves more like that shown in Figure 1A. Figure 1A shows noise only, but serves to illustrate that the baseline in chromatography slopes upwardly over time. Therefore, the first step of the present method is to adjust the baseline of the data signal to zero. The important aspect of this step is that, first, when adjusting the baseline the relevant time information must be retained, and, secondly, the noise portion of the data signal must be numerically centered about the zero baseline, as can be seen in FIG. 1B.

The next step involves integrating the zero baseline adjusted data signal again preserving corresponding time information for each point of the data signal. Examples of the integration of the data signals or chromatograms of FIG. 2 can be seen in FIG. 3. It will be noticed that the scales of FIGS. 3A, B and C are different to facilitate better comparison. The stepped portions 20a–e of the integrated chromatograms of FIG. 3 correspond to the peaks 10a–e of the normal original chromatograms in FIG. 2. It can be obviously seen that detectability is greatly enhanced especially for the hard to detect chromatogram of FIGS. 2C and 3C.

FIGS. 4A, B and C represent integrated chromatograms having the same peak data but different noise data.

Figure 3:
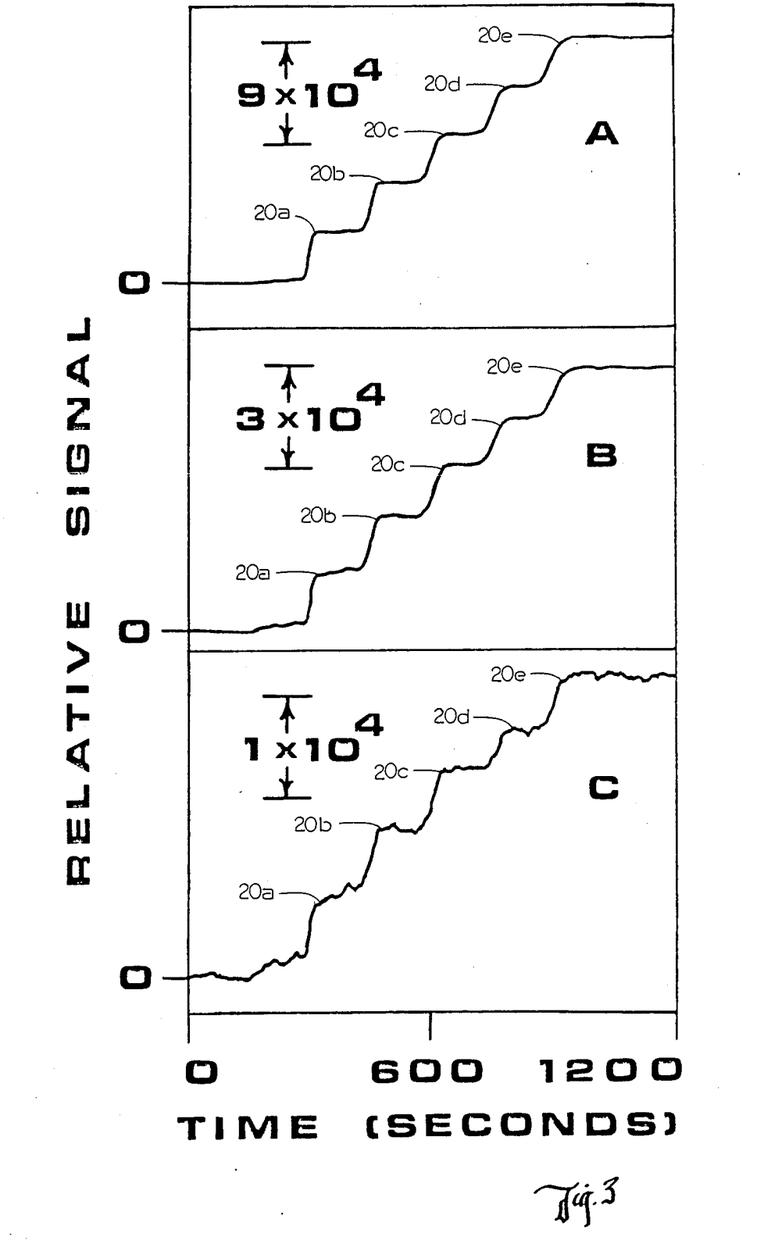
Figure 5:
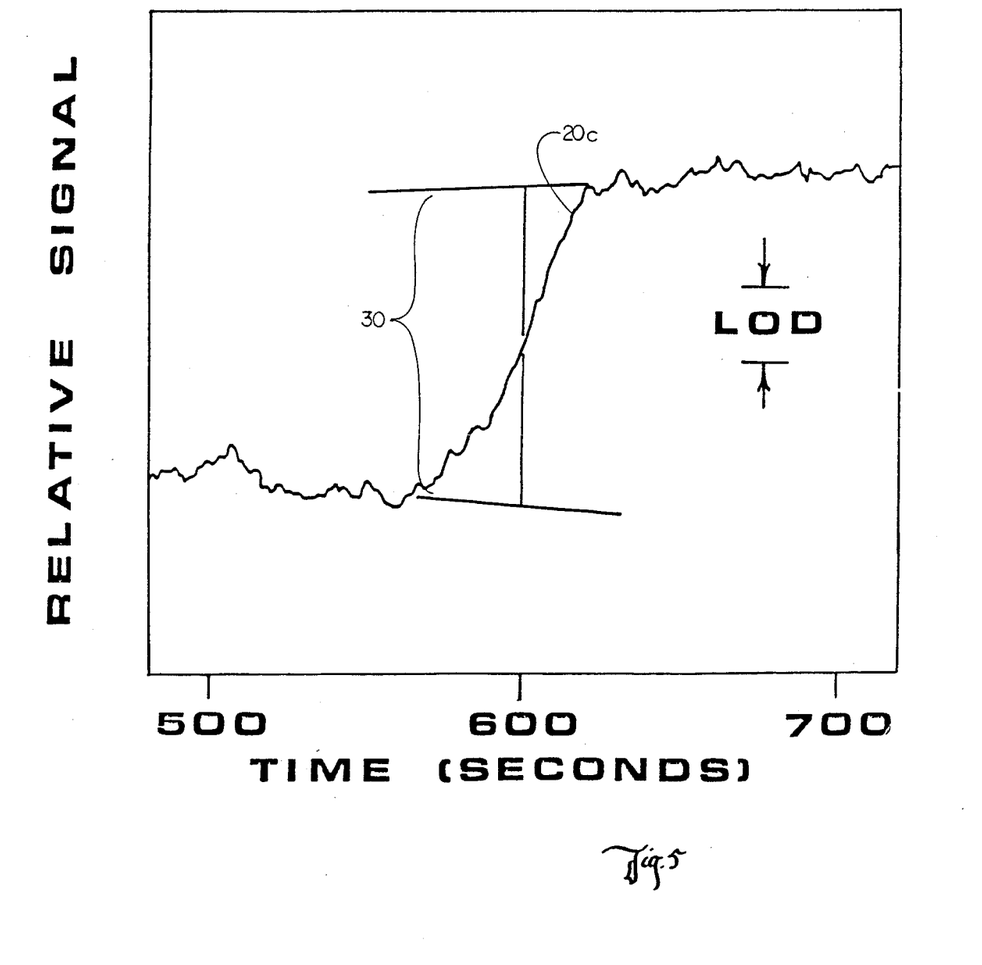
FIG. 5 is a representation of the quantification of a signal in an integrated chromatogram, for a given portion of the chromatogram showing the improved limit of detection (LOD).

The correlation of the integrated chromatogram for each species is determined by the method shown in FIG. 5. The integrated chromatograms of FIG. 3 are statistically analyzed to determine the exact location in correlation with the abscissa for placing the peak representing that particular species of the sample. FIG. 5 shows schematically the limit of detection (LOD) for a particular segment of the integrated chromatogram corresponding to the 500 to 700 second segment with stepped portion 20C. As can be seen, the upward sloping portion 30 is far greater than the limit of detection thus insuring accuracy and reliability in an analysis of the chromatogram.

The method of the invention is accomplished by first obtaining a collection of the data set comprising the chromatogram or chromatographic record. This data set is stored in a computer such as a PDP 11/10 Mini Computer (manufactured by Digital Equipment Corporation, Maynard, Mass.). The baseline adjustment to a zero reference and the integration procedures are then performed by the computer producing the enhanced integrated data signal improving the limit of detection. The data processing steps are carried out through the software program as can be written by those of ordinary skill in the art utilizing the conventional equations and operations used herein. All such computations are based upon equations and calculations known within the art. The data processing software generates integrated chromatograms similar to those shown in FIGS. 3–5 and additionally completes the analysis process by determining the species contained in the sample and their quantities, all within the improved limit of detection, increasing the accuracy and information obtained from the chromatographic process.

To further describe the invention, experimental testing of the method of the invention will now be described, showing its resulting improvement in the limit of detection.

Computer simulation was used to test the method of the invention. To understand the analysis which follows, the relationship of the area of a chromatographic peak to the maximum height of the same chromatographic peak must be defined and described. The simulating computer generated Gaussian peak shape models, but this procedure can similarly be applied to other peak shapes. Each chromatographic peak i in a chromatogram can be described by $$S_i(t) = \frac{V_i R_i}{\sigma_i \sqrt{2\pi}} \exp\left( \frac{-(t - t_{R,i})^2}{2\sigma_i^2} \right) \quad (1)$$

where $S_i(t)$ is the height of the peak i at time t, defined by the standard deviation of the peak ($\sigma_i$), retention time ($t_R$) at the maximum $S_i(t)$, volume fraction injected ($v_i$), and analyte detection response factor ($R_i$). An exponentially modified Gaussian (EMG) function would be preferred to model a chromatographic peak over a Gaussian model, however, the Gaussian model is adequate.

By integrating equation (1), the area of a chromatographic peak ($S_{i,AREA}$) can be calculated:

$$S_{i,AREA} = \int_{-\infty}^{+\infty} S_i(t)dt = \quad (2a)$$

$$\int_{-\infty}^{+\infty} \frac{V_i R_i}{\sigma_i \sqrt{2\pi}} \exp\left( \frac{-(t - t_{R,i})^2}{2\sigma_i^2} \right) dt$$

where integration from ($t_{R,i} - 3\sigma_i$) to ($t_{R,i} + 3\sigma_i$) is sufficient in recovering 99.74% of the total area. It is to be understood that $$\int_{-\infty}^{+\infty} \frac{1}{\sigma_i \sqrt{2\pi}} \exp\left( \frac{-(t - t_{R,i})^2}{2\sigma_i^2} \right) dt = 1 \quad (2b)$$

Since $V_i$ and $R_i$ are independent of time the following is derived $$S_{i,AREA} = V_i R_i \quad (2c)$$

By substituting $t = t_{R,i}$ into equation (1), the maximum signal $S_{i,MAX\ HT}$) of a chromatographic peak can be calculated, $$S_{i,MAX\ HT} = \frac{V_i R_i}{\sigma_i \sqrt{2\pi}} \quad (3)$$

In conventional chromatographic systems, the maximum signal ($S_{i,MAX\ HT}$) is used to determine detectability. Again, detectability for conventional systems means that $S_{i,MAX\ HT}$ must be greater than a confidence value determined by considering the noise of the background in order for peak i to be detectable. However, by using only the $S_{i,MAX\ HT}$ of a peak for the purpose of deciding detectability, much of the "implicit" correlation about a chromatographic peak is wasted. The present method utilizes the entire peak and its area rather than just the maximum signal. The result is a signal increase factor (SIF) which is the result of dividing equation 2c by equation 3, $$SIF = \frac{S_{i,AREA}}{S_{i,MAX\ HT}} = \sigma_i \sqrt{2\pi} \quad (4)$$

(no consideration of background noise is incorporated into equation (4)).

The standard deviation for each peak ($\sigma_i$) is related to retention in a typical chromatographic system by $$\sigma_i = \left( \frac{t_0^2}{r} [k_i(1 + k_i)] \right)^{\frac{1}{2}} \quad (5)$$

where r is a constant for a given chromatographic system independent of analyte or retention time, and $k_i$ is the capacity factor for peak i and is defined as follows, $$k_i = \frac{t_{R,i} - t_0}{t_0} \qquad (6)$$

with $t_0$ equal to the dead time, typically around 150 seconds. In equation (5), r is on the order of 1000 to 2000 for liquid chromatograhy and $\sigma_i$ is calculated in units of time. It is noted that SIF calculated in equation (4), which is effectively the chromatographic dilution factor for a given peak, is also in units of time.

Information about the chromatographic baseline F(t) is expressed as a linear combination as follows, $$F(t) = mt + b + D(t) + R(t) + N_t \qquad (7)$$

where m is the slope of linear baseline drift, t is the time, b is the y-intercept of a baseline chosen at t=0 ($t_{inject}$), D(t) is any non-linear and essentially non-repeating baseline fluctuation such as temperature effects, R(t) is any non-linear yet repeating baseline fluctuation such as electronic ringing or pump pulsation effects, and $N_t$ is the random noise associated with a physical measurement that can be statistically treated. Sampling a large population of $N_t$ values should yield Gaussian statistics for Gaussian experimental noise, which is frequently observed for chromatography detectors.

Figure 1:
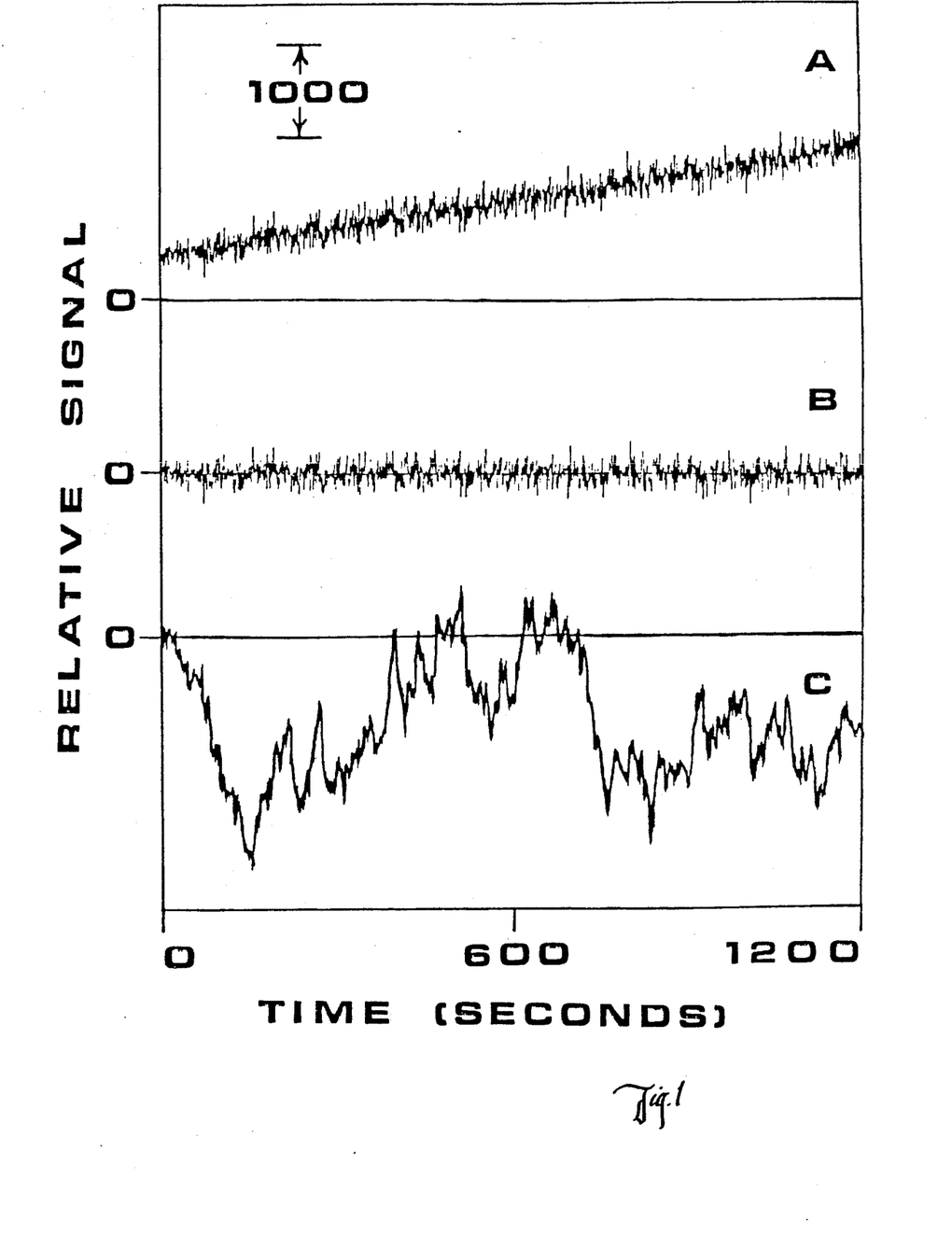

It is to be noted that both D(t) and R(t) in equation (7) can be reduced to near zero and thus neglected in equation (7) by proper experimental consideration and procedure. For any chromatographic system there is a portion of time before any material elutes ($t_{inject}$ to $t_0$), and a portion of time after any material will elute (ca K'>7 or so). By doing a linear least-squares fit to these two portions of a chromatogram, the slope (m*) and y-intercept (b*) (at t=$t_{inject}$) can be calculated to good precision. A baseline adjusted (BLA) chromatogram can be calculated by taking equation (7) (neglecting D(t) and R(t)) and sequentially subtracting the slope-intercept contribution, $$F^*(t) = F(t) - m^*t - b^* = N_t \qquad (8)$$

for t=1, 2, 3 ..., n−1, n for a n-point chromatogram. In the present example, n equals 1200, and each increment of t denotes one second in time. 1200 is selected for its convenience of providing a 20 minute chromatogram with a 1 second time constant. Integration (i.e. addition) of noise should produce a value that remains close to the mean value of F*(t) before integration, which should be approximately equal to zero. To understand this, reference should be had to FIG. 1 which displays an example of equations (7), (8), and (9). An integrated baseline (IBL) at each time interval t (i.e. data point) in a chromatogram is given as follows, $$IBL(t) = \sum_{t=1}^{t} F^*(t) = \sum_{t=1}^{t} N_t \qquad (9)$$

where IBL(t) is the running-total integration of F*(t). FIG. 1A represents a typical baseline noise which is not baseline adjusted (equation (7)). FIG. 1B is a representation of equation (8), that being baseline adjusted noise (that is, around a zero reference baseline). FIG. 1C represents equation (9) showing integrated baseline adjusted noise. It is important to note that a baseline adjusted to be centered about zero is necessary to have the IBL stay close to zero. Although the integrated baseline adjusted noise in FIG. 1C appears to be larger in magnitude than the normal baseline in FIGS. 1A and B, integration of the signal and the chromatogram relative to a normal chromatogram more than compensates for this increase. It is to be understood that for the IBL, the units for the vertical scale are actually "Relative Signal×Time" and not just the "Relative Signal", as is the case for the normal baseline. Further, equation (9) is a running-total expression and not a running-average. Using a running-total will not decrease the resolution (i.e, separation information) of closely eluting chromatographic peaks since no averaging of information is done.

Next, determination of confidence limits for the IBL chromatogram are obtained by calculating the standard deviation of baseline fluctuations for the time-span chosen to be 60 data points (i.e. seconds), which approximates the time span of an "event" of chromatographic elution. First, the average value (u) of a section j of a baseline can be calculated by, $$u_j = \frac{\left[ \sum_{t=t_b}^{t_f} X(t) \right]}{p} \qquad (10)$$

with j=1, 2, 3, 4 ..., m−1, m, and p=60 such that $(m) \times (p) = 1200$, and with $t_b = 1 + ((j-1)p)$ and $t_f = p + ((j-1)p)$.

Then, the standard deviation ($\sigma$) for each baseline section can be calculated by, $$\sigma_j = \left( \frac{\sum_{t=t_b}^{t_f} (X_t - u_j)^2}{p - 1} \right)^{\frac{1}{2}} \qquad (11)$$

for j=1, 2, 3 ..., m−1, m, and with $t_b$ and $t_f$ as in equation (10), and $$\overline{\sigma}_x = \frac{\left( \sum_{j=1}^{m} \sigma_j \right)}{m} \qquad (12)$$

for m sections of length p, where t is the index synonymous with time. From equation (12), $\overline{\sigma}_x$ is the average standard deviation of a "series" of blank or background measurements in general form. For a BLA chromatogram, $\overline{\sigma}_x = \sigma_N$ is calculated using equations (10)–(12) with X(t)=F*(t). For the integrated BLA chromatogram, $\overline{\sigma}_x = \sigma_I$ is calculated similarly with X(t)=IBL(t).

In the absence of any peaks, a comparison of the baseline noise for a normal chromatographic baseline and an integrated chromatographic baseline can be made by relating $\sigma_N$ and $\sigma_I$. Assuming the same number of standard deviations is used in defining detectability, a noise increase factor (NIF) can be defined as $$NIF = \frac{\sigma_I}{\sigma_N} \qquad (13)$$

Equation (13) should adequately describe the theoretical relationship between the noise in a normal chromatogram and the noise in the integrated chromatogram. NIF will be greater than 1.

Next, by referring to FIG. 2, the simulation of a "real" chromatogram containing peaks and baseline is shown. The convolution of chromatographic peaks with baseline noise to form a chromatogram is made by combining equation (1) and equation (7). Thus, a simulated normal chromatogram C(t) is produced by, $$C(t) = S(t) + F(t) \tag{14}$$

C(t) is a sequential array of elements with several peaks. Each peak (indexed by i) is defined by a retention time ($t_{R,i}$) and a peak width ($\sigma_i$, equation (5) and equation (6)). The baseline adjusted chromatograms of FIG. 2 can be shown as, $$C(t) = \left[ \frac{V_i R_i}{\sigma_i \sqrt{2\pi}} \exp\left( \frac{-(t - t_{R,i})^2}{2\sigma_i^2} \right) \right] + N_t \tag{15}$$

The exponential part essentially vanishes for $|t - t_{R,i}| > 3\sigma_i$. Also, $N_t$ represents the random baseline noise.

Integration of the chromatograms of equation (15) produces an integrated chromatogram I(t) shown by, $$I(t) = \sum_{t=1}^{t} C(t) \tag{16}$$

where I(t) is the running-total integration of C(t).

The testing of the present invention seeks to compare the detectability between C(t) and I(t). An improvement factor (IMP) for the integrated chromatogram relative to the normal chromatogram can be calculated using equations (4), (5), (6), and (13) as follows, $$IMP = \frac{SIF}{NIF} = \frac{\sigma_N}{\sigma_I} \left[ \frac{2\pi}{r} (t_{R,i}^2 - t_0 t_{R,i}) \right]^{\frac{1}{2}} \tag{17}$$

The value of IMP increases as the retention time increases, showing greater improvement for later eluting peaks compared to earlier eluting peaks. The constant r decreases as the efficiency of a column decreases, suggesting that the poorer the column, the better the improvement (larger IMP). The value of IMP is independent of any data averaging that might be applied to a chromatogram. However, it is important to have a chromatogram that has enough points to maintain the chromatographic information for the resolution of closely eluting species, and to achieve good precision in the final quantitation. This is realized experimentally by detecting the event with an instrument that has an appropriate time constant. As a suggested minimum, the width (c) of the earliest chromatographic peak should be at least 10 time constant intervals. Then, a data collection rate the same as the detector time constant will produce the optimum IMP possible for a given detector time constant. The ratio $\sigma_N/\sigma_I$ is determined empirically by characterizing the detected background noise (without injection).

Chromatographic simulation, quantitation and statistical calculations were all done on a PDP 11/10 minicomputer by Digital Equipment Corporation. All software was written inhouse except for the utilization of a pseudo-random number generator designed specifically for a 16-bit computer. The pseudo-random number generator produces numbers evenly distributed between 0 and 1, so the distribution was transformed into a normal distribution (Gaussian) by a suitable method. The noise generated was treated statistically, and the distribution was found to be Gaussian by calculating the fraction of noise for a population between one, two, and three standard deviations. The equations utilized in the simulation of the chromatograms have been previously discussed.

Experimental noise was collected for two sets of conditions. To insure that problems due to long-term fluctuations would not affect the data, a 10 millisecond data collection rate (to produce a 1200 point data set) was used. A 12 second baseline was produced. An Amperex (North American Philips), 56-DYP photomultiplier tube was operated at either 1500 volts (room lights on) or 2100 volts (room lights off) with a Hamner (Princeton, N.J.), Model Nv-13-P, high voltage power supply. The photomultiplier tube output signal was sent into a Princeton Applied Research (Princeton, N.J.), Model HR-8 lock-in amplifier with termination at 100ΩK. A 10 millisecond output time constant was used with a 100 KHz measurement lock-in frequency supplied by a Wavetek (San Diego, Calif.) Model 162 wave generator. The signal output from the lock-in amplifier was collected by the computer with a LPS-11 laboratory interface at a 10 millisecond data collection rate. The resulting data files were analyzed and found to also show a Gaussian distribution.

Statistical comparison of simulated chromatograms to normal chromatograms will now be discussed. It is important to understand that the improvement in detectability between a normal and an integrated chromatogram is found in the relative values.

The first step in verifying the improvement in detectability for the present invention is to calculate a "working" NIF equation (13). This is done by statistical analysis of three baseline noise chromatograms (without peaks), as shown in Table I below.

TABLE I

| | Typical Baseline Noise Data | | | |
|---|---|---|---|---|
| | Normal Chrom | | Int. Chrom. | |
| Interval (Sec.) | $u_j^{(a)}$ | $\sigma_j^{(b)}$ | $u_j^{(c)}$ | $\sigma_j^{(d)}$ |
| 1–60 | −7.61 | 73.51 | −231.72 | 199.34 |
| 61–120 | −21.08 | 96.30 | −1190.20 | 448.92 |
| 121–180 | 1.05 | 98.66 | −2046.08 | 248.78 |
| 181–240 | −1.49 | 95.48 | −1415.66 | 299.04 |
| 241–300 | 3.93 | 108.55 | −1420.20 | 295.80 |
| 301–360 | 5.66 | 105.40 | −1307.92 | 230.81 |
| 361–420 | 11.57 | 100.48 | −729.67 | 396.52 |
| 421–480 | 6.98 | 105.72 | −290.26 | 280.69 |
| 481–540 | −8.37 | 100.44 | −150.69 | 394.25 |
| 541–600 | −2.93 | 101.99 | −700.70 | 210.88 |
| 601–660 | 16.55 | 99.63 | 23.39 | 239.18 |
| 661–720 | −7.30 | 104.04 | −20.96 | 189.35 |
| 721–780 | −21.41 | 96.21 | −1247.43 | 392.38 |
| 781–840 | −1.52 | 107.97 | −1556.82 | 253.66 |
| 841–900 | 1.05 | 85.03 | −1495.66 | 102.61 |
| 901–960 | 8.01 | 102.39 | −1004.27 | 207.81 |
| 961–1020 | −2.91 | 113.15 | −1024.23 | 302.38 |
| 1021–1080 | −4.07 | 106.42 | −1069.80 | 196.50 |
| 1081–1140 | 2.48 | 92.39 | −1517.20 | 195.25 |
| 1141–1200 | 0.73 | 90.26 | −1052.04 | 150.25 |
| AVE $\bar{\sigma}_x^{(e)}$ | | 99.20 | | 261.72 |

[a] eq 10, × (i) = F*(t).
[b] eq 11, × (i) = F*(t).
[c] eq 10, × (i) = IBL(t).
[d] eq 11, × (i) = IBL(t).
[e] eq 12.

Table I contains the results of applying equations (10), (11), and (12) to the normal and integrated chromatograms for typical baseline noise, that is, Gaussian noise in the normal chromatogram. Visually, a normal baseline (FIG. 1A) should be baseline adjusted (BLA) and appears like FIG. 1B, while an integrated baseline appears as in FIG. 1C. By analyzing two more baselines similar to the one in Table I, the $\sigma_N$ was found to be 99.67 ($\pm 0.38$) and $\sigma_I$ was 274.13 ($\pm 31.82$). The important quantity is the ratio $\sigma_I/\sigma_N$, namely, NIF=2.78.

Simulation of chromatographic peaks should suggest realistic column performance. A typical value for the column performance constant in equation (5) and equation (17) is r = 1500, along with $t_o$=150 seconds. Simulated chromatographic peak data was calculated using equations (1), (2), and (3) to form "noise-free" chromatograms (see Table II below).

TABLE II
True Data and Theoretical Improvement Factor (IMP) for Simulated Chromatograms

| Peak Number | Peak $t_R$ (Sec) | Max Height (a) | Area (b) | IMP (theoretical) (Sec) (c) |
| --- | --- | --- | --- | --- |
| 1 | 300 | 364.2 | 5000.0 | 4.94 |
| 2 | 450 | 210.3 | 5000.0 | 8.55 |
| 3 | 600 | 148.7 | 5000.0 | 12.10 |
| 4 | 750 | 115.2 | 5000.0 | 15.62 |
| 5 | 900 | 94.0 | 5000.0 | 19.13 |

(a) eq 3 and eq 5 with $t_O$ = 150 sec, $R_i$ = 5 × $10^6$, $V_i$ = 1.0 × $10^{-3}$.
(b) eq 2C with $R_i$ = 5 × $10^6$, $V_i$ = 1.0 × $10^{-3}$.
(c) eq 17 using $\sigma_I/\sigma_N$ = 2.78, $t_O$ = 150 sec and r = 1500.

Five well-resolved peaks were generated such that each analyte has the same detector response factor ($R_i$), such as with an indirect mode detector. Volume fractions are chosen for the purpose of discussion, and should be used only to compare the normal and integrated chromatograms. The theoretical IMP factors are shown in Table II, suggesting a marked improvement in detectability in the integrated chromatogram. Notice that the improvement increases with increased retention time. This is because the integration method compensates for the band broadening effect due to chromatographic retention.

Once the above results have been found, baseline noise and chromatographic peak data are combined or convoluted to produce a simulated "real-life" chromatogram via equation (15). FIG. 2 shows simulated chromatograms for excessive dilutions of a sample. The peak data given in Table II correspond to the BAA chromatogram shown in FIG. 2C. Note that the detectability does not appear very favorable, especially for the later eluting peaks in FIG. 2C.

By performing the running-total integration of the data in FIGS. 2A–2C using equation (16), integrated chromatograms are obtained. The results are shown in FIG. 3. Note the vertical scale used for each integrated chromatogram relative to the scale used in FIG. 2. The improvement in detectability in the integrated chromatograms relative to the normal chromatograms is obvious.

Figure 4:
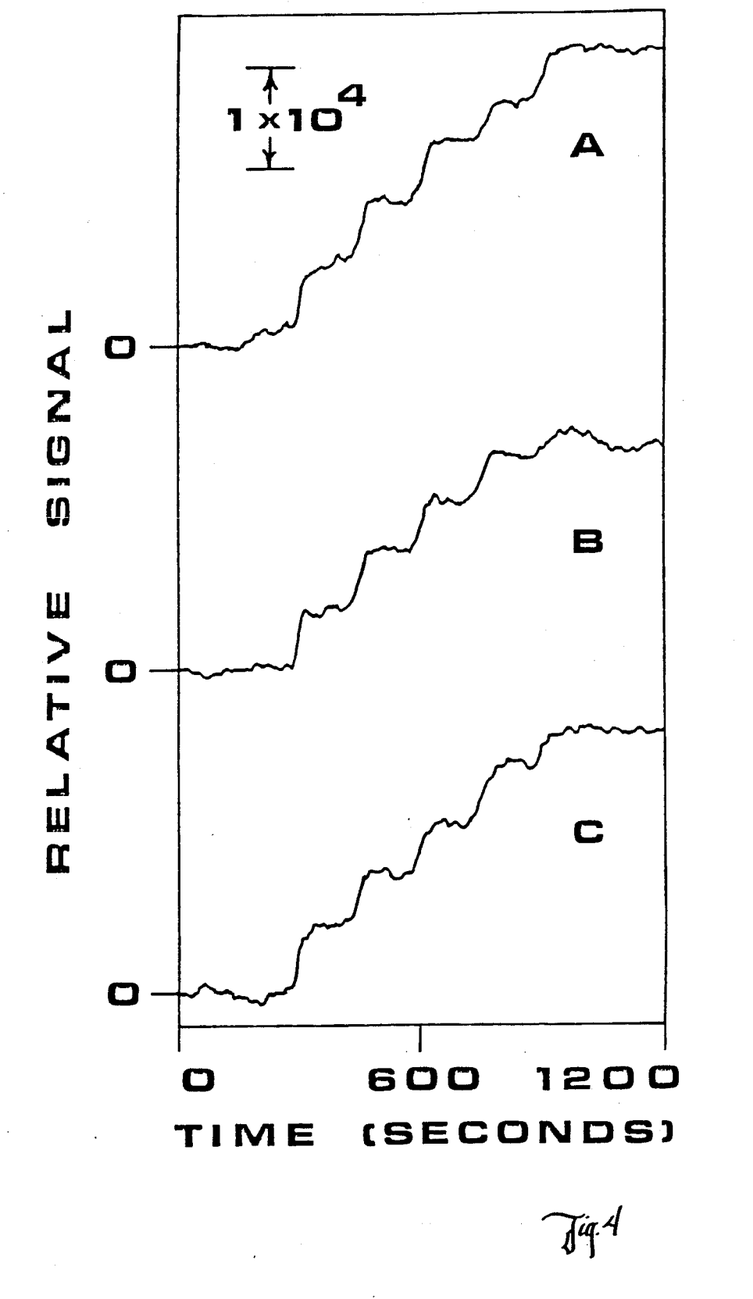

The precision and accuracy that the present method of the invention provides compared to conventional procedures, is tested by simulating multiple injections via a fixed S(t) in equation (14), but varying the baseline noise function F(t) In doing so it is assumed that no uncertainty in $V_i$ exists, so the uncertainties in quantitation due only to the data handling can be studied. Three integrated chromatograms using equation (16) on three different C(t) arrays for the same "sample" are shown in FIG. 4. Note that FIG. 4A is for the same sample as FIG. 3C.

The signal of this integration method is determined by first calculating the value of $\sigma_I$, as previously explained. From this value, a limit of detection (LOD) for the integrated domain can be calculated as some number (typically 5) multiplied by $\sigma_I$. Deflections in an integrated chromatogram exceeding this LOD constitute an analytical signal. For a given analytical signal, a region on each side of the signal relatively close to having a slope of zero will be observed as can be seen in FIG. 5. The quantity corresponding to the LOD, $5\sigma_I$, is shown for convenience. Since the slope may not be exactly zero in the two regions on either side of the signal, a least-squares linear regression is calculated for each section. The extrapolated linear regression lines are shown for the signal in FIG. 5. The distance between the two lines at the inflection point of the analytical signal curve is the area of the original chromatographic peak, and thus, the signal of the analyte in the integrated chromatogram.

By deriving the relative standard deviation (RSD) the precision of the analytical method of the invention can be quantified. The standard deviation for the quantitation of three trials ($\sigma_Q$) relative to the average for the three trials (Q), multiplied by 100, will be used, $$RSD\% = \left(\frac{\sigma_Q}{Q}\right)100\% \tag{18}$$

The accuracy of the method of the invention is derived by comparing the true value (T), given in Table II, relative to the average of the three trials (Q). A relative difference of these two quantities can be calculated by, $$RD\% = \left(\frac{Q-T}{T}\right)100\% \tag{19}$$

Note that the sign is important for this quantity in comparing analytical methods.

To give some measure of comparison for the precision and accuracy of the method of the invention, three other analytical methods used to quantitate chromatographic data will now be compared to the integration method of the invention. Method I employs defining the peak height as the measurement of the largest signal on an interval in a normal chromatogram known to contain a peak, but exact knowledge of the retention time is not know. Method II also determines the peak height in a normal chromatogram, but the retention time must be known to the same precision as the data acquisition rate. In Method II the peak height is measured at precisely the retention time, thus, not necessarily providing the largest signal for a given peak. Method III provides the peak area by summing the signals in a normal chromatogram, but only those signals greater than or equal to some confidence level. This method, in essence, treats each data point as a separate event, and suggests no implicit correlation of the data for an eluting chromatographic peak. For Method III, only those data points greater than $3\sigma_N$ are added to the total for given peak. For purposes of the present discussion, the integration method of the present invention will be referred to as Method IV.

Results were obtained for the application of the four quantitation methods for the three samples shown in FIG. 2, using three arbitrarily chosen baseline noise arrays.

The standard deviation ($\sigma_Q$) of the three signals obtained for a given peak were calculated, and the "true" values were known (Table II) so equations (18) and (19) could be applied. The results for studying precision are given in Table III (below), while the accuracy data is given in Table IV (below).

TABLE III

| | Precision (RSD %) for Average Three Trials | | | |
|---|---|---|---|---|
| Peak Number | Max Ht[b] ($t_R$ Not Assumed) | Height @ $t_R$[c] | Peak Area[d] | This Work[e] |
| Sample 1[a] | | | | |
| 1 | 7.4 | 14.0 | 3.4 | 8.3 |
| 2 | 6.4 | 59.5 | 19.1 | 6.8 |
| 3 | 11.7 | 46.6 | 39.2 | 8.6 |
| 4 | (f) | (f) | (f) | 18.8 |
| 5 | (f) | (f) | (f) | 20.8 |
| Sample 2[a] | | | | |
| 1 | 3.9 | 4.5 | 5.5 | 2.8 |
| 2 | 7.5 | 18.2 | 4.4 | 2.4 |
| 3 | 6.0 | 12.0 | 4.3 | 3.0 |
| 4 | 5.4 | 45.1 | 6.4 | 6.4 |
| 5 | 8.7 | 16.3 | 32.5 | 6.2 |
| Sample 3[a] | | | | |
| 1 | 1.4 | 1.5 | 0.68 | 0.94 |
| 2 | 2.8 | 5.9 | 1.3 | 0.83 |
| 3 | 2.4 | 3.7 | 2.4 | 1.0 |
| 4 | 0.47 | 10.6 | 2.5 | 2.1 |
| 5 | 8.5 | 6.2 | 1.9 | 2.0 |

[a] Peak Number as in Table II Sample 1: $V_i = 1 \times 10^{-3}$; Sample 2: $V_i = 3 \times 10^{-3}$ Sample 3: $V_i = 9 \times 10^{-3}$; Samples 1, 2 and 3: $R_i = 5 \times 10^6$
[b] Method I.
[c] Method II.
[d] Method III.
[e] Method IV.
[f] Undefined, since $\sigma_Q > Q$.

TABLE IV

| | Relative % Difference (RD %) from True Value for Average of Three Trials | | | |
|---|---|---|---|---|
| Peak Number | Max Ht[b] ($t_R$ Not Assumed) | Height @ $t_R$[c] | Peak Area[d] | This Work[e] |
| Sample 1[a] | | | | |
| 1 | +38.4 | −4.2 | −53.0 | +1.3 |
| 2 | +82.1 | −12.0 | −84.1 | +11.8 |
| 3 | +134.7 | −30.7 | −86.6 | +9.8 |
| 4 | (f) | (f) | (f) | +2.8 |
| 5 | (f) | (f) | (f) | −14.2 |
| Sample 2[a] | | | | |
| 1 | +10.3 | −1.3 | −6.8 | +0.43 |
| 2 | +22.7 | −3.9 | −15.9 | +3.9 |
| 3 | +43.0 | −10.3 | −30.8 | +3.3 |
| 4 | +50.8 | −38.4 | −50.0 | +0.92 |
| 5 | +62.7 | +24.1 | −71.1 | −4.7 |
| Sample 3[a] | | | | |
| 1 | +2.3 | −0.45 | −0.91 | +0.14 |
| 2 | +6.7 | −1.3 | −3.9 | +1.3 |
| 3 | +12.3 | −3.4 | −5.8 | +1.1 |
| 4 | +14.0 | −12.8 | −8.4 | +0.31 |
| 5 | +16.7 | +8.0 | −16.3 | +1.6 |

(a)–(f) Same as Table III

The following comparisons relative to Method IV can be made from the data of these two tables. Method I clearly produces a signal that is very inaccurate, biased to higher values compared to the true values, although the precision is reasonably good. Method II has no expected bias, but the precision and the accuracy are both relatively poor. Because of the confidence level criterion imposed upon Method III, the peak area is substantially less than the true values. The precision of Method III is comparable to Method IV, except at low volume fractions. In general, the predicted improvement in detectability (IMP, equation (17)) is substantiated by the observations made from Tables III and Iv. For Sample 1, the peaks at 750 and 900 seconds cannot be quantitated by Methods I–III, while the new integration method (Method IV) works quite well. It is interesting to note that the signals shown in FIG. 4, together with statistics given in Tables III and IV (Sample 1, Method IV), are at an average signal-to-noise (S/N) of 7.30. For this system at the LOD (S/N=2), a volume fraction of $2.74 \times 10^{-4}$ is calculated. Comparatively, the other three methods are essentially useless even at a volume fraction of $1 \times 10^{-3}$.

Because the success of this integration method is strongly dependent upon the behavior of the original baseline, comparison was made to a few experimentally obtained "real" noise arrays. A few typical detection systems were studied and the results supported the data previously provided by the simulation.

The importance of minimizing the effects of D(t) and R(t) in equation (7) through proper experimental consideration can not be emphasized enough. In applying this integration method, it is essential to use the baseline adjustment procedure. Once baseline adjusted, it is a simple task to generate the running-total integrated chromatogram from a normal chromatogram. Similar to any other quantitative method, rejection of spurious results can be made by proper statistical tests. That is, anomalous features in an integrated chromatogram can be dealt with just as is conventionally done in a normal chromatogram for such things as glitches, pseudopeaks, impurity peaks, etc. This integration method should give better LOD values, that are essentially independent of chromatographic dilution effects. Furthermore, this method can be readily incorporated into typical data handling systems currently in use for chromatography. Finally, the method should have general applicability for any data set in which the experimental noise, be it Gaussian or otherwise, is uncorrelated along a given abscissa and an analytical signal is correlated along the same abscissa. The abscissa may be time, wavelength, frequency, etc.

Figure 7:
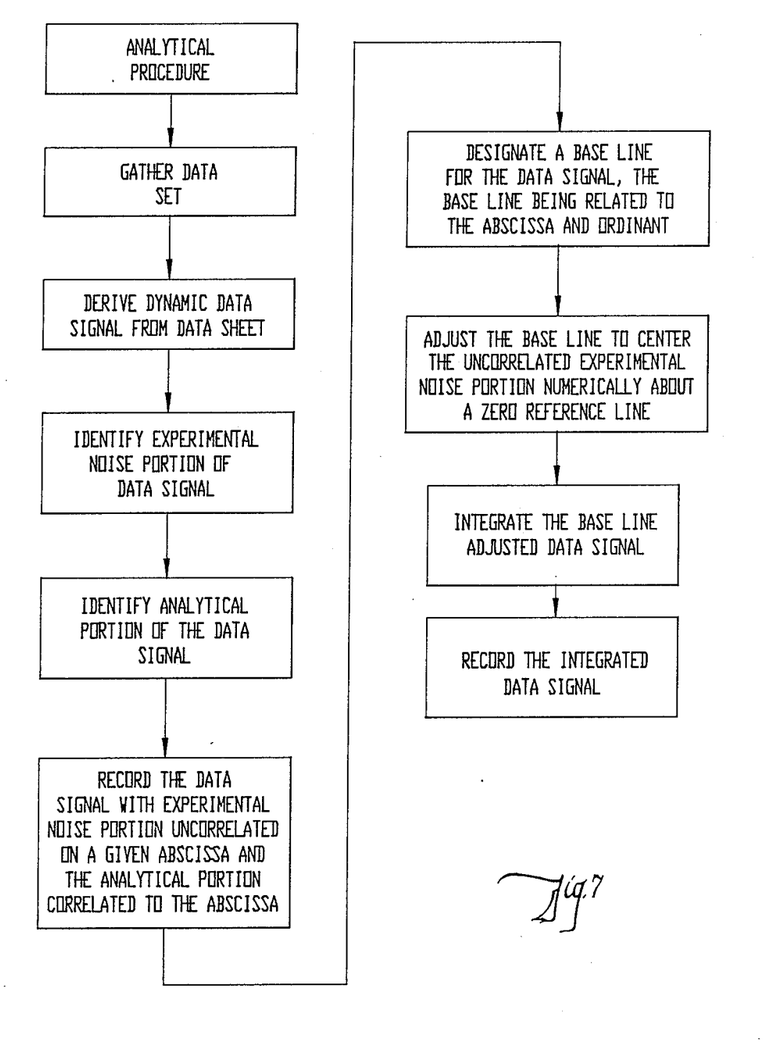
FIG. 7 is a flowchart of the method steps of a preferred embodiment of the present invention.

FIG. 7 sets forth in diagrammatic or flowchart from, the method steps of a preferred embodiment of the invention, such as previously described.

Figure 8:
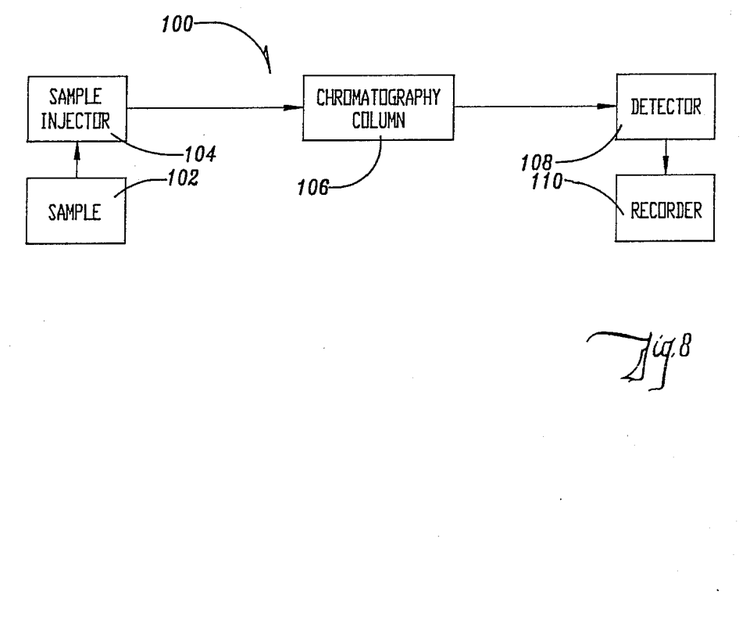
FIG. 8 is a diagrammatical view of a chromatography means for deriving a data signal from an analytical procedure, namely chromatography.

As is well known in the art, FIG. 8 depicts a diagrammatical view of a chromatographic apparatus 100. A sample or material 102 to be chromatographically analyzed is submitted to sample injector 104. By means well known within the art, injector 104 injects sample 102 into a chromatography column 106. A detector 108, such as is well known in the art, produces a signal corresponding to what occurs in the chromatography column 108. The signal of detector 108 comprises the data set and data signal for that analytical procedure. It contains an analytical portion and an experimental noise portion. Recorder 110 is then utilized to record the signal from detector 108.

The included preferred embodiment is given by way of example only, and not by way of limitation to the invention, which is solely described by the claims herein. Variations obvious to one skilled in the art will be included within the invention defined by the claims.

Figure 6:
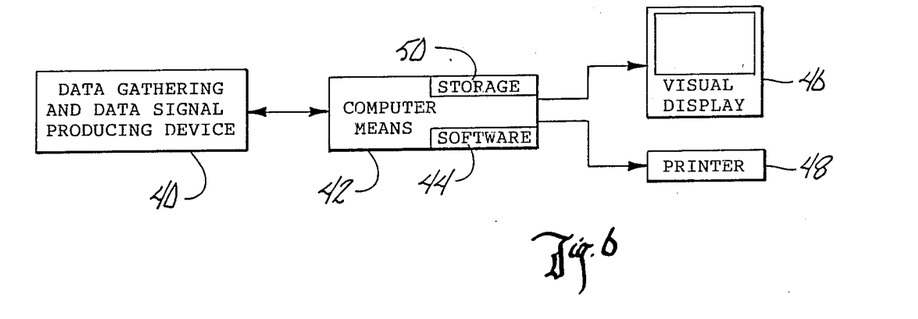
FIG. 6 schematically depicts one possible arrangement of means to accomplish the invention.

For example, FIG. 6 schematically depicts one arrangement of means for practicing the invention. A data gathering and data signal producing device 40 serves to derive the desired data from a chosen event or events, and then converts, produces, or represents the data as a signal. A computer means 42 and computer software 44, such as are known in the art, communicate with device 40 to operate upon the data signal according to the present invention, as previously described. The results of the process can optionally be shown on a visual display means 46, printed out in hard copy on printer 48, or stored in storage 50 of computer means 42, such as is known within the art.

What is claimed is:

1. A method for improving limit of detection for a data set represented in a dynamic data signal derived from an analytical procedure in which an experimental noise portion of the data signal is uncorrelated to a given abscissa and an analytical portion of the data signal is correlated to said abscissas, comprising:

collecting, in recorded form on a record means, said data signal by monitoring with detector means at least one analytical procedure, involving analytical equipment and material to be analyzed, to gather said data set, and converting said data set into said data signal which includes said analytical portion and said experimental noise portion;

with the data signal in collected and recorded form, designating a base line for said data signal after observation of the data signal;

adjusting said base line of said data signal to center said experimental noise portion numerically about a zero reference line while preserving correlation to the abscissa; and integrating said data signal, after base line adjustment, and preserving corresponding correlated abscissa information for each point of said data signal, said integration producing an enhanced integrated data signal, in recorded form on a record means, with respect to the adjusted base line while causing said experimental noise portion to be minimized, improving said limit of detection.

2. The method of claim 1 wherein the analytical portion comprises a chromatogram.

3. The method of claim 2 wherein the analytical portion comprises chromatographic signals.

4. The method of claim 1 further comprising the step of storing the data set after collecting the data set.

5. The method of claim 1 further comprising the step of storing the integrated data signal after integrating the data signal for processing by a computer.

6. The method of claim 1 wherein after the step of integrating the data signal, the data signal is stored and operated upon by computer means to achieve an output corresponding to the data set with improved detectability.

7. The method of claim 1 wherein a computer means is used to operate on the data set, to center the baseline about zero, and integrate the data signal.

8. The method of claim 7 further comprising visually displaying the data signal after integration.

9. The method of claim 7 wherein the computer means prepares a record of desired information from the data signal after integration.

10. The method of claim 1 wherein the step of adjusting the baseline to center the experimental noise about a zero reference comprises baseline subtraction from a least-squares statistical method involving slope and Y-intercept approach using baseline sections.

11. The method of claim 1 wherein the integration of the data signal comprises a running-total summation with all time information preserved.

* * * * *